United States Patent
Cronstein et al.

(10) Patent No.: US 6,555,545 B2
(45) Date of Patent: Apr. 29, 2003

(54) ADENOSINE $A_{2A}$ RECEPTOR ANTAGONISTS FOR TREATING AND PREVENTING HEPATIC FIBROSIS, CIRRHOSIS AND FATTY LIVER

(75) Inventors: Bruce N. Cronstein, New York, NY (US); Edwin Chan, New York, NY (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 09/780,365

(22) Filed: Feb. 12, 2001

(65) Prior Publication Data

US 2002/0002145 A1 Jan. 3, 2002

Related U.S. Application Data

(60) Provisional application No. 60/181,546, filed on Feb. 10, 2000.

(51) Int. Cl.[7] ............ A61K 31/519; C07D 239/00; C07H 19/20
(52) U.S. Cl. ............ 514/261; 514/46; 514/258; 514/262; 514/263; 514/266; 544/242; 544/239; 544/253; 544/256; 544/262; 544/264; 544/265; 536/26.13
(58) Field of Search ............ 514/261, 258, 514/263, 266, 262, 46; 544/242, 239, 253, 256, 262, 264, 265; 536/26.13

(56) References Cited

U.S. PATENT DOCUMENTS

| | | | |
|---|---|---|---|
| 4,705,658 A | 11/1987 | Lukas | |
| 4,968,697 A | 11/1990 | Hutchison | |
| 5,036,381 A | 7/1991 | Hutchison et al. | |
| 5,063,233 A | 11/1991 | Chen et al. | |
| 5,426,101 A | 6/1995 | Peet et al. | |
| 5,599,671 A | 2/1997 | Jacobson et al. | |
| 5,859,019 A | 1/1999 | Liang et al. | |
| 5,877,180 A | * 3/1999 | Linden et al. | 514/266 |
| 5,916,910 A | 6/1999 | Lai | |
| 5,932,558 A | 8/1999 | Cronstein et al. | |
| 6,211,165 B1 | * 4/2001 | Liang et al. | 514/46 |
| 6,232,297 B1 | * 5/2001 | Linden et al. | 514/46 |
| 6,303,619 B1 | * 10/2001 | Linden | 514/263 |

FOREIGN PATENT DOCUMENTS

WO    9850047    11/1998

OTHER PUBLICATIONS

Hernandez–Munoz et al., "Adenosine partially prevents cirrhosis induced by carbon tetrachloride in rats." Hepatology (Baltimore 12(2), 242–248, 1990.*

Cronstein, et al., "Adenosine: A Physiologic Modulator of Superoxide Anion Generation by Human Neutrophils, Adenosine Acts via an $A_2$ Receptor on Human Neutrophils," The Journal of Immunology, 1985, 1366–1371, 135(2), U.S.A.

(List continued on next page.)

Primary Examiner—James O. Wilson
Assistant Examiner—Devesh Khare
(74) Attorney, Agent, or Firm—Browdy and Neimark, P.L.L.C.

(57) ABSTRACT

Hepatic cirrhosis and fibrosis and fatty liver can be prevented and treated by administering to a subject in need thereof an effective amount of at least one adenosine $A_{2A}$ receptor antagonist or at least one adenosine uptake promotor.

11 Claims, 5 Drawing Sheets

OTHER PUBLICATIONS

Salmon, et al., "Fcy Receptor–Mediated Functions in Neutrophils are Modulated by Adenosine Receptor Occupancy: A1 Receptors are Stimulatory and A2 Receptors are Inhibitory," The Journal of Immunology, 1990, 2235–2240, 145(7), U.S.A.

Cronstein, et al., "Adenosine: an Endogenous Inhibitor of Neutrophil–mediated Injury to Endothelial Cells," J. Clin. Invest., 1986, 760–770, 78, U.S.A.

Cronstein, et al., "Methotrexate inhibits neutrophil function by stimulating adenosine release from connective tissue cells," Proc. Natl., Acad. Sci. USA, 1991, 2441–2445, 88, U.S.A.

Rose, et al., "Adenosine Promotes Neutrophil Chemotaxis," J. Exp. Med., 1988, 1186–1194, 167, U.S.A.

Anand–Srivastava, et al., "Presence of 'Ra' and 'P'–Site Receptors for Adenosine Coupled to Adenylate Cyclase in Cultured Vascular Smooth Muscle Cells," Biochemical and Biophysical Research Communications, 1982, 213–219, 108(1).

Ralevic, et al., "Receptors for Purines and Pyrimidines," Pharmacological Reviews, 1998, 413–492, 50(3).

Abstract of Blackburn, et al., "The use of enzyme therapy to regulate the metabolic and phenotypic consequences of adenosine deaminase deficiency in mice. Differential impact on pulmonary and immunologic abnormalities," J. Biol. Chem., 2000, 32114–21, 275(41).

Abstract of Corrao, et al., "The effect of drinking coffee and smoking cigarettes on the risk of cirrhosis associated with alcohol consumption.A case–control study. Provincial Group for the Study of Chronic Liver Disease," Eur. J. Epidemiol., 1994, 657–64, 10(6).

Klatsky, et al., "Coffee, Tea and Mortality," Ann. Epidemiol., 1993, 375–381, 3.

Boyle, et al., "Inhibition of Synoviocyte Collagenase Gene Expression by Adenosine Receptor Stimulation," Arthritis & Rheumatism, 1996, 923–930, 39(6).

Puig, et al., "Ethanol–induced Activation of Adenine Nucleotide Turnover Evidence for a Role of Acetate," J. Clin. Invest., 1984, 936–941, 74.

Smail, et al., "In Vitro, *Candida albicans* Releases the Immune Modulator Adenosine and a Second, High–Molecular Weight Agent that Blocks Neutrophil Killing," The Journal of Immunology, 1992, 3588–3595, 148.

Dubey, et al., "Adenosine Inhibits Collagen and Protein Synthesis in Cardiac Fibroblasts, Role of $A_{2B}$ Receptors," Hypertension, 1998, 943–948, 31.

Stiles, "Adenosine Receptors," The Journal of Biological Chemistry, 1992, 6451–6454, 267(10).

Tanaka, et al., "Coffee Consumption and Decreased Serum Gamma–Glutamyltransferase and Aminotransferase Activities Among Male Alcohol Drinkers," International Journal of Epidemiology, 1998, 438–443, 27.

Schrier, et al., "The Effects of Adenosine Agonists on Human Neutrophil Function," The Journal of Immunology, 1986, 3284–3289, 137.

Ramkumar, et al., "Demonstration of Both $A_1$ and $A_2$ Adenosine Receptors in $DDT_1$ MF–2 Smooth Muscle Cells," Molecular Pharmacology, 1989, 149–156, 37.

Van Calker, et al., "Adenosine Regulates via Two Different Types of Receptors, the Accumulation of Cyclic AMP in Cultured Brain Cells," J. Neurochem, 1979, 999–1005, 33.

Stiles, "Adenosine Receptors: Structure, Function and Regulation," Trends in Pharmacol. Sci., 1986, 486–490, 7.

Jarvis, et al., "[$^3$H ]CGS 21680, A Selective $A_2$ Adenosine Receptor Agonist Directly Labels $A_2$ Receptors in Rat Brain," The Journal of Pharmacology and Experimental Therapeutics, 1989, 888–893, 251(3).

Abstract of Iannone, et al., Human Neutrophils Possess Adenosine $A_2$ Receptors, Fed. Proc., 1985, 580, 44.

Jacobson, et al., "Adenosine Receptors: Pharmacology, Structure–Activity Relationships, and Therapeutic Potential," Journal of Medicinal Chemistry, 1992, 407–422, 35(3).

Herlihy, et al., "Adenosine Relaxation of Isolated Vascular Smooth Muscle," American Journal of Physiology, 1976, 1239–1243, 230.

Berne, "The Role of Adensine in the Regulation of Coronary Blood Flow," Circ. Res., 1980, 807–813, 47.

Anand–Srivastava, et al., "Stimulation of Adenylate Cyclase by Adenosine and other Agonists in Mesenteric Artery Smooty Muscle Cells in Culture," Life Sciences, 1985, 857–867, 37.

Barrington, et al., "Identification of the $A_2$ Adenosine Receptor Binding Subunit by Photoaffinity Crosslinking," Proc. Natl. Acad. Sci, USA, 1989, 6572–6576, 86.

Barrington et al., "Glycoprotein Nature of the $A_2$–Adenosine Receptor Binding Subunit," Molecular Pharmacology, 1990, 177–183, 38.

Klatsky, et al., "Alcohol, Smoking, Coffee, and Cirrhosis," American Journal of Epidemiology, 1992, 1248–57, 136.

Khakh, et al., "Adenosine and ATP: progress in their receptors' structures and functions," Trends in Pharmacological Sciences, 1998, 39–41, 19(2).

Londos, et al., "Subclasses of External Adenosine Receptors," Proc. Natl. Acad. Sci, USA, 1980, 2551–2554, 77(5).

Olah, et al., "Adenosine Receptors," Annu. Rev. Physiol., 1992, 211–25, 54.

Norris, et al., "Androgen Receptors in a Syrian Hamster Ductus Deferens Tumor Cell Line," Nature, 1974, 422–424, 248.

Salvatore, et al., Disruption of the A3 Adenosine Receptor Gene in Mice and Its Effect on Stimulated Inflammatory Cells, Journal of Biological Chemistry, 2000, 4429–4434, 275(6).

Frederiksen, "Specificity of Adenosine Deaminase Toward Adenosine and 2'–Deoxyadenosine Analogues," Archives of Biochemistry and Biophysics, 1966, 383–388, 113.

Hirschhorn, "Adenosine Deaminase Deficiency: Molecular Basis and Recent Developments," Clincial Immunology and Immunopathology, 1995, S219–S227, 76(3).

Chen, et al., "$A_{2A}$ Adenosine Receptor Deficiency Attenuates Brain Injury Induced by Transient Focal Ischemia in Mice," The Journal of Neuroscience, 1999, 9192–9200, 19(21).

* cited by examiner

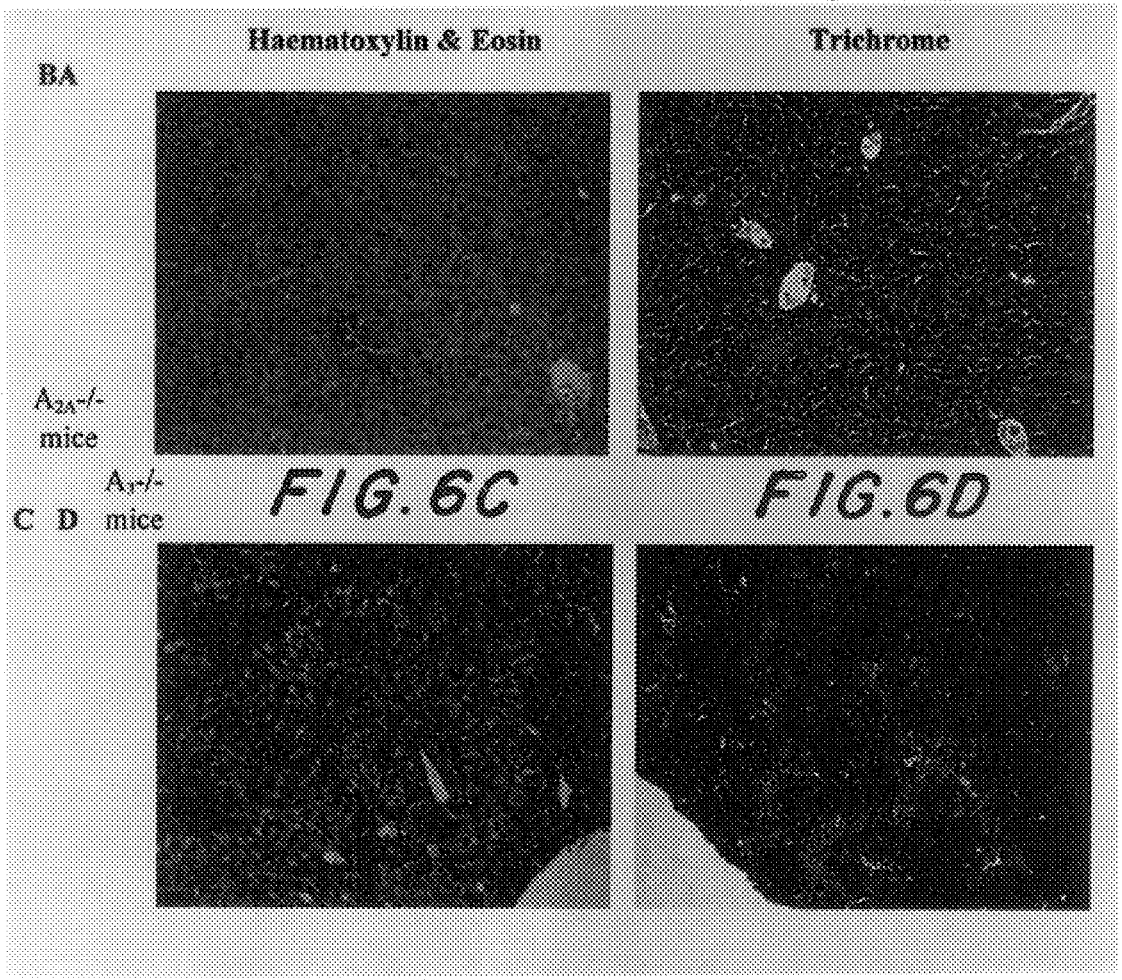

ADENOSINE A$_{2A}$ RECEPTOR ANTAGONISTS FOR TREATING AND PREVENTING HEPATIC FIBROSIS, CIRRHOSIS AND FATTY LIVER

REFERENCE TO OTHER APPLICATIONS

The present application claims priority from provisional application Ser. No. 60/181,546, filed Feb. 10, 2000, the entire contents of which are hereby incorporated by reference.

FIELD OF THE INVENTION

The present invention relates to methods and compositions for treating and preventing hepatic fibrosis and cirrhosis as well as fatty liver.

BACKGROUND OF THE INVENTION

Adenosine is a nucleoside with wide distribution in the body. Adenosine mediates a broad array of physiological responses, including central nervous system sedation, inhibition of platelet aggregation and vascular smooth muscle vasodilation. These effects occur largely through interaction of adenosine with one of four types of adenosine receptors.

Adenosine thus perhaps represents a general regulatory substance, since no particular cell type or tissue appears uniquely responsible for its formation. In this regard, adenosine is unlike various endocrine hormones. There is no evidence for storage and release of adenosine from nerve or other cells. Thus, adenosine is unlike various neurotransmitter substances.

Adenosine, like the prostaglandins, may be characterized as a physiological regulator. In both cases the enzymes involved in the metabolic formation are ubiquitous and appear to be responsive to alterations in the physiological state of the cell. Receptors for adenosine, like those for prostaglandins, are very widespread.

Adenosine receptors comprise a group of cell surface molecules that mediate the physiologic effects of adenosine. Recent reviews include Stiles, G. F., *Trends in Pharmacol. Sci.* 7:485–490 (1986); Ramkumar, V. et al.,*Prog. Drug Res.* 32:195–247 (1988); Olah, M. E. et al., *Anu. Rev. Physiol.* 54:211–225 (1992); Stiles, G. L. *J. Biol. Chem.* 267:6451–6454 (1992); Jacobson, K. A. et al., *J. Med. Chem.* 35:407–422 (1992). This family of receptors was originally classified as P1 or P2 purinergic receptors, dependent upon their preferential interactions with adenosine (P1) or ATP (P2) (Burnstock et al., in *Cell Membrane Receptors of Drugs and Hormones*, Straub et al., eds., Raven Press, New York, 1978, pp. 107–118). The P1 sites were further subdivided into $A_1$, $A_{2A}$, $A_{2B}$, and $A_3$ adenosine receptors based on their differential selectivity of adenosine analogues and molecular structure (Van Calker, D. et al.,*J. Neurochem* 33:999–1005 (1979); Londos, C. et al. *Proc. Natl. Acad. Sci. USA* 77:2552–2554 (1980); Ralevic et al., *Pharmacological reviews* 50(3):413–92 (1998); Poulsen et al., *Bioorganic & Medicinal Chemistry* 6(6):619–41 (1998); Khakh et al., *Trends in Pharmacological Sciences*19(2): 39–41 (1998)). The $A_1$ adenosine receptor, which is inhibitory to adenylyl cyclase, exhibits the potency order (R)-PIA>NECA>(S)-PIA. The $A_2$ adenosine receptor, which is stimulatory to adenylyl cyclase, has a different potency order were NECA>(R)-(PIA)>(S)-PIA. ((R)-PIA is N6-phenylisopropyladenosine; (S)-PIA is N6-(S)-phenylisopropyladenosine; NECA is N-ethyl adenosine-5'-uronic acid). Both the $A_1$ and the $A_2$ adenosine receptors are widely distributed in the central nervous system and peripheral tissues (Ramkumar, V. et al., supra).

Additional information on adenosine receptors can be found in Ralevid et al., *Pharmacological reviews* 50(3): 413–92, 1998; Poulsen et al., *Bioorganic & Medicinal Chemistry* 6(6):619–41, 1998 and Khakh et al., *Trends in Pharmacological Sciences* 19(2):39–41, 1998.

Four different adenine receptors have been claimed and their sequence is known. Until relatively recently, no truly useful radio ligand was available for characterizing the $A_2$ adenosine receptors. Demonstration of adenosine receptors in smooth muscle was made primarily by functional assays, for example, adenosine stimulation of adenylyl cyclase activity via $A_2$ receptors in vascular smooth muscle cells in culture (Anand-Srivastava, M. B. et al., *Biochem. Biophys. Res. Commun.* 108: 213–219 (1982); Anand-Srivastava , M. B. et al., *Life Sci.* 37: 857–867 (1985)). However, the concentrations of adenosine required to elevate cAMP were higher than those required of full vasorelaxation in vivo (Berne, R. M., *Circ. Res.* 47:807–813 (1980); Herlihy, J. T. et al., *Am. J. Physiol.* 230:1239–1243 (1976)). One cell line which has proved useful of studying A1 and A2 adenosine receptors (Ramkumar, V. et al., *Molec. Pharmacol.* 37:149–156 (1990) is the DDT1 MF-2 line, a smooth muscle cell line derived from a steroid-induced leimyosacroma of the vas deferens of an adult Syrian hamster (Norris, J. S. et al., *Nature* 248:422–424 (1974)).

Recently, two compounds were found to possess selective high affinity against radio ligands of the $A_2$ receptor: [3H] CGS 21680 (Jarvis, M. R. et al., *J. Pharmacolo. Exp. Their* 251:888–893 (1989) and 125I-PAPA-APEC, the full chemical name of which is {2-3(2(2-(4-amino phenyl)methyl carbonyl-amino)ethylaminocarbonyl)ethyl] phenyl}ethylamino-5'-N-ethylcarboxamindoadenosine (Barrington, W. W. et al., *Proc. Natl. Acad. Sci. USA* 86:6572–6576 (1989)). Use of such ligands allowed identification of the $A_2$ binding subunit as a 45 kDa protein (on SDS-PAGE) that was clearly distinguishable from the 38 kDa $A_1$ binding subunit. Use of the azide derivative of $^{125}$I-PAPA-APEC, a direct photo affinity probe of the $A_2$ receptor, made it possible to demonstrate that the $A_2$ binding subunit is a glycoprotein clearly different from the $A_1$ receptor glycoprotein (Barrington, W. W. et al., *Mol. Pharmacol.* 38:177–183 (1990)). The $A_2$ adenosine receptor has a single carbohydrate chain of either the complex or high mannose type.

Useful adenosine receptor agonists, in particular those with selectivity of the $A_2$ receptor, are well known in the art. These include 2-substituted adenosine-5'-carboxamide derivatives (Hutchison, U.S. Pat. Nos. 4,968,697 and 5,034, 381) and N9-cyclopentyl-substituted adenine derivatives (Chen et al., U.S. Pat. No. 5,063,233). These patents are hereby incorporated by reference in their entireties.

Adenosine and its analogues interact with neutrophils in inflammatory responses. While neutrophils are essential for limiting the spread of infection by a variety of microbes, stimulated neutrophils may damage injured tissues while en route to sites of infection or inflammation. Release of adenosine is one mechanism by which normal cells may protect themselves from activated neutrophils. Thus, one important action of adenosine and its analogues is the inhibition of generation of toxic oxygen products, including $O_2^-$ and $H_2O_2$, by interacting with $A_2$ receptors on the neutrophil (Cronstein, B. N. et al., *J. Immunol.* 135:1366–1371 (1985); Roberts, P. A. et al., *Biochem. H.* 227:669–674 (1985); Schrier, D. J. et al., *J. Immunol.*

137:3284–3289 (1989); Iannone, M. A. et al., *Fed. Proc.* 44:580 (abstr.) (1985)). Adenosine promotes neutrophil chemotaxis via the $A_1$ receptor (Cronstein, B.Nalet supra; Rose, F. R. et al., *J. Exp. Med.* 167:1186–1194 (1989)). Adenosine receptor ligation regulates inflammatory responses of neutrophils triggered by immune complexes acting through the Fcγ receptor (Salmon, J. E., *Immuno.* 145:2235–2240 (1990)). Specifically, activation of $A_2$ receptors inhibited these inflammatory responses, whereas activation of $A_1$ receptors was stimulatory. These authors noted an important role of adenosine at picomolar concentrations as a promoter, and at micro molar concentrations as an inhibitor, of neutrophil responses elicited by immune complexes.

Interestingly, the immunosuppressive drug methotrexate, at low concentrations, acts as an anti-inflammatory agent at least in part due to its capacity to induce adenosine release by connective tissue cells such as dermal fibroblasts or umbilical vein endothelial cells. The released adenosine interacted with the neutrophil adenosine receptors (Cronstein, B. N. et al., *Proc. Natl. Sci. USA* 88:2441–2445 (1991)).

The nonselective adenosine receptor agonist, 2-chloroadenosine, inhibited adherence of stimulated neutrophils to endothelium, thus protecting the endothelium from inflammatory effects (Cronstein, B. N. et al., *J. Clin, Invest.* 78:760–770 (1986)). More recently, work from the present inventors' laboratory has demonstrated that occupancy of $A_2$ receptors inhibits neutrophil adherence and generation of toxic metabolites, thus contributing to an anti-inflammatory function (Cronstein, B. N. et al. *J. Immunol.* 148:2201–2206 (1992)).

The present inventors have thus found that adenosine regulates the accumulation of neutrophils at sites of inflammation. While neutrophils traverse through acellular connective tissue, the low concentrations of adenosine present promote phagocytosis, migration, and adherence to some, but not other, surfaces. Near foci of tissue injury, damaged cells release higher concentrations of adenosine that inhibit neutrophil adherence to cells and connective tissue substrata as well as inhibiting production of toxic oxygen metabolites by stimulated neutrophils. Thus, adenosine may promote accumulation of neutrophils at sites of tissue injury or microbial invasion, a pro-inflammatory function (Cronstein et al., 1992, supra)

It has been demonstrated that adenosine $A_{2A}$ receptor agonists promote wound healing. Enhanced dermal wound healing is accompanied by increased matrix (collagen) in the wounds. Cronstein et al., in U.S. Pat. No. 5,932,558, the entire contents of which are hereby incorporated by reference, disclose the use of adenosine receptor agonists for promoting wound healing. Increased adenosine release mediates many of the anti-inflammatory effects of methotrexate treatment, and the present inventors investigated whether methotrexate-stimulated adenosine release might also contribute to the methotrexate-induced hepatic fibrosis that occurs in a small number of patients.

A number of epidemiological studies have demonstrated that coffee consumption protects from development of cirrhosis: Lepore et al., "The Effect of Drinking Coffee and Smoking Cigarettes on the Risk of Cirrhosis Associated with Alcohol Consumption," *European Journal of Epidemiology* 10(6):657–664, 1994; Klatsky et al., "Coffee, Tea and Immortality," *Annals of Epidemiology* 3(4):375–381, 1993; Klatsky et al., "Alcohol, Smoking, Coffee, and Cirrhosis," *American Journal of Epidemiology* 136(10):1248–1257, 1992; Tanaka et al., "Coffee Consumption and Decreased Serum Gamma-Glutamyltransferase and Aminotransferase Activities Among Male Alcohol Drinkers," *International Journal of Epidemiology* 27(3):438–443, 1998.

Caffeine, an ingredient in coffee, is a relatively nonselective adenosine receptor antagonist. The effects of caffeine on wakefulness, heart rate, etc., are all due to its capacity to block adenosine receptors. In recent epidemiological studies, coffee consumption appears to protect against the development of alcoholic cirrhosis, and one of the more prominent pharmacologic components of coffee is caffeine, a non-selective adenosine receptor antagonist (Lepore A. R. et al., *European J. Epicemiol.* 10(6):657–664 (1994).

Pharmacologically relevant concentrations of methotrexate and ethanol and combinations thereof caused increased adenosine release from HepG2 cells (a hepatoma cell line) in multiple experiments. The present inventors have observed in a number of experiments that CGS-21680, a relatively selective adenosine $A_{2A}$ receptor agonist, promotes collagen synthesis and release from a cultured rat stellate cell line in a dose-dependent fashion ($EC_{50}$ approximately 300 nM) by as much as 20-fold ($p<0.004$). CSC, a specific adenosine $A_{2A}$ receptor antagonist almost completely blocks the CGS-21680-mediated promotion of collagen synthesis and release. DPCPX, an adenosine $A_1$ receptor antagonist, and enprofylline, an $A_{2B}$ receptor antagonist, have little effect on the capacity of CGS-21680 to stimulate collagen release and synthesis.

Liang et al., in U.S. Pat. No. 5,859,019, describe methods for protecting against cardiac ischemia by administering adenosine $A_{2A}$ receptor antagonists, particularly 8-(3-chlorostyryl) caffeine, to patients suffering from ischemic damage or at risk for the same.

There is currently no treatment of the progression of development of liver fibrosis or cirrhosis or fatty liver other than antiviral therapy, which prevents underlying hepatic destruction.

SUMMARY OF THE INVENTION

It is an object of the present invention to overcome the aforesaid deficiencies in the prior art.

It is another object of the present invention to treat liver fibrosis, cirrhosis, or fatty liver.

It is a further object of the present invention to prevent liver fibrosis, cirrhosis, or fatty liver.

According to the present invention, agonists for adenosine $A_{2A}$ receptors promote synthesis of collagen by stellate cells. Antagonists at these receptors prevent the agonist-mediated increase in collagen synthesis. During tissue injury or necrosis, or after exposure to ethanol, the hepatocytes release high concentrations of adenosine, which may stimulate production of collagen in the liver, leading to hepatic fibrosis and cirrhosis. Thus, administration of adenosine $A_2$ receptor antagonists can block promotion of collagen synthesis and release, and thus prevent and treat hepatic fibrosis, cirrhosis, or fatty liver.

BRIEF DESCRIPTION OF THE DRAWINGS

FIG. 6 comprises photomicrographs of adenosine $A_{2A}$ receptor-deficient mice protected against carbon tetrachloride-induced liver fibrosis.

DETAILED DESCRIPTION OF THE INVENTION

The present inventors recently demonstrated that adenosine $A_{2A}$ receptor agonists promote wound healing, cf. in U.S. Pat. No. 5,932,558, the entire contents of which are hereby incorporated by reference. Enhanced dermal wound healing is accompanied by increased matrix (collagen) in the wounds. Increased adenosine release mediates many of the anti-inflammatory effects of methotrexate treatment.

Methotrexate Induces Adenosine Production in HepG2 Cells

Since adenosine mediates the anti-inflammatory action of methotrexate and is released from multiple cell types, studies were conducted to determine whether methotrexate induces adenosine release from cells in the liver parenchyma. HepG2 cells, a human hepatoma cell line (gift from Dr. A. B. Reiss) were grown to confluence and incubated for three hours with 0–10 mM methotrexate at 37° C. in 5% $CO_2$. Adenosine extraction and quantitation by HPLC were performed using methods described in Smail et al., *J. Immunol.* 1992; 148(11):3588–95.

Figure 1:
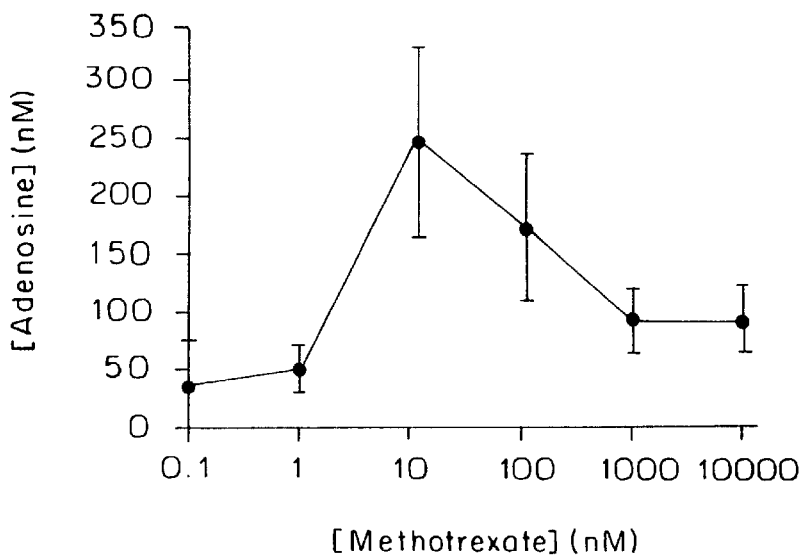
FIG. 1 shows concentrations of methotrexate and ethanol causing increased adenosine release from HepG2 cells.

As shown in FIG. 1, increased adenosine release was observed with increasing methotrexate concentrations up to 10 nM, which serum concentrations are achievable with anti-inflammatory doses of methotrexate used in rheumatic diseases. At higher doses of methotrexate, which diminish cellular proliferation, adenosine release diminishes, as do the number of cells present in the cultures. At a methotrexate concentrations of 10 nM, adenosine release was increased six-fold, from 41±39 nM to 242±82 nM, control, vs. MTX, n=6, p<0.001.

Ethanol Induces Adenosine Production in HePG2 Cells

Ethanol is known to potentiate the risk of development of liver cirrhosis with methotrexate treatment, and patients on methotrexate are customarily advised to abstain from alcohol consumption. Ethanol is a well-recognized independent risk factor for the development of cirrhosis in its own right, and alcohol-induced cirrhosis has a much greater health impact worldwide compared to methotrexate-induced hepatic fibrosis. Therefore, the effect of ethanol on adenosine release in hepatocytes was investigated.

Figure 2:
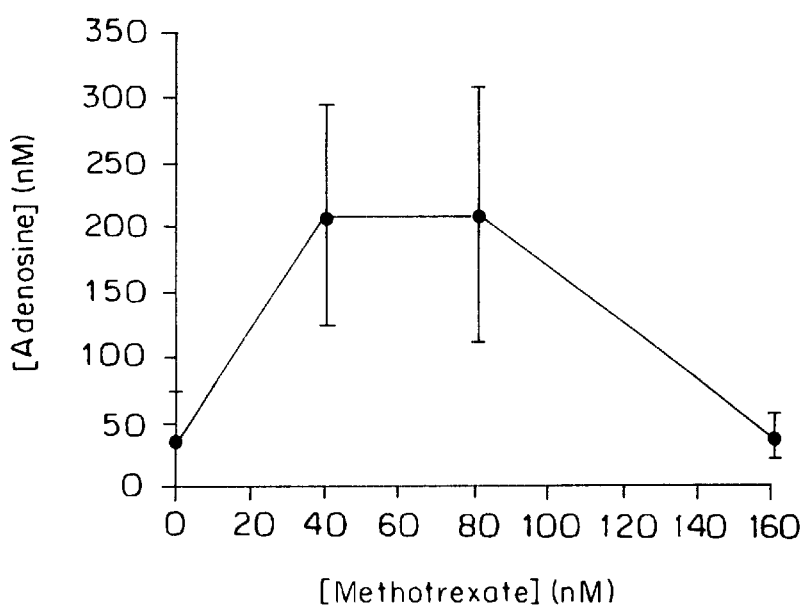
FIG. 2 illustrates adenosine production in HepG2 cells by ethanol.

HepG2 cells were incubated for three hours with ethanol at concentrations o0–160 mg/dl at 37° C., 5% $CO_2$. A serum level of 80 mg/dl is the legal driving limit of ethanol in most jurisdictions. Adenosine was quantitated as above. It was found that ethanol concentrations of up to 80 mg/dl promote adenosine release from HepG2 cells. Concentrations of ethanol greater than this are toxic to HepG2 cells, consistent with the decrease in adenosine release observed, as shown in FIG. 2. Incubation of methotrexate-treated HepG2 cells with ethanol further increased adenosine release at relevant concentrations of methotrexate, and the effects of methotrexate and ethanol on adenosine release appear to be additive (data not shown). At an ethanol concentration of 40 mg/dl, adenosine release is increased four-fold from control (from 37±35 nM to 206±79 nM, control, vs. MTX, n=6, p<0.001). These findings are consistent with previous demonstrations that ethanol increases ATP breakdown and purine release into the extracellular space in human subjects, Piug et al., *J. Clin. Invest* 1984; 74(3):936–41.

The Adenosine $A_{2A}$ Receptor Agonist, CGS-21680, Increases Collagen Production by Rat and Human Hepatic Stellate Cells (rHSC and LX-1)

Figure 3:
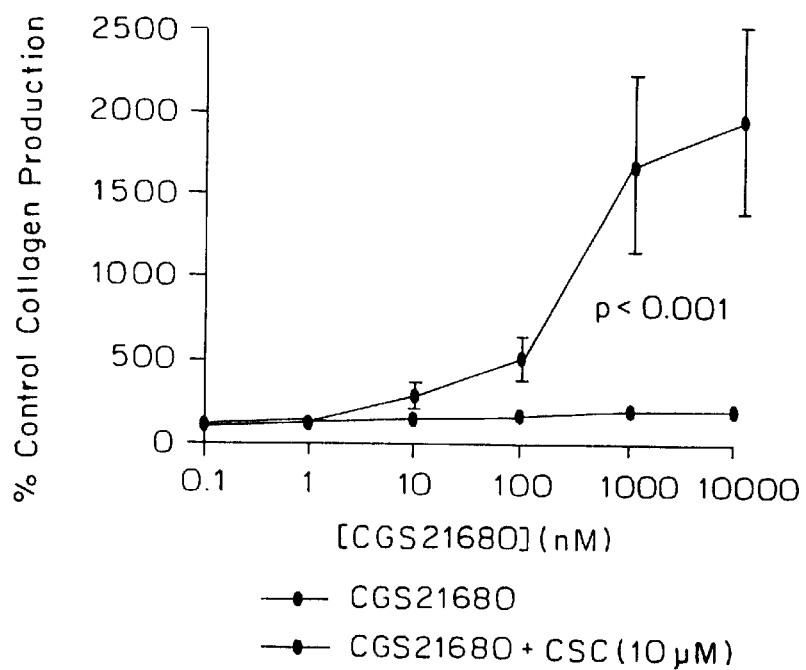
FIG. 3 illustrates that the adenosine $A_{2A}$ receptor agonist, CGS-21680, increases collagen production by rHSC.
Figure 4:
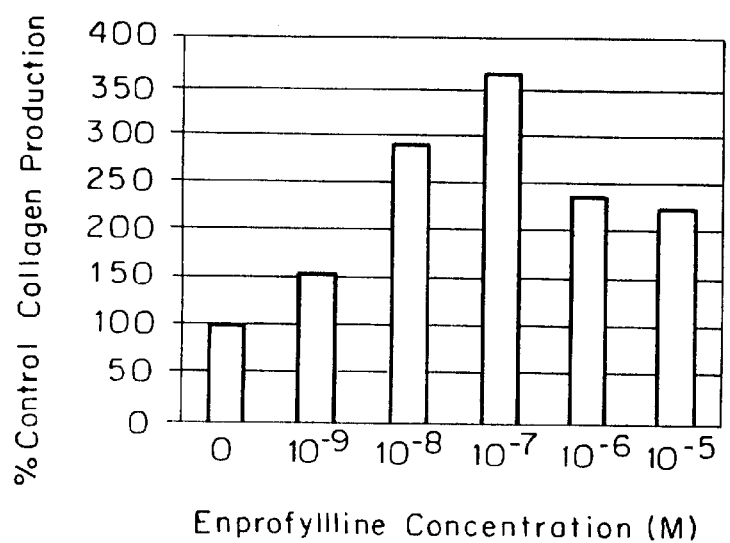
FIG. 4 illustrates that the adenosine $A_{2A}$ receptor agonist, CGS-21680, alters collagen production by Human stellate cells (LX-1 cell line).

To determine whether an increase in adenosine release would promote collagen production, immortalized rat hepatic stellate cells (rHSC, gift from Dr. S. L. Friedman) were incubated with agonists and antagonists at various adenosine receptors, after which collagen production was quantitated. Rat hepatic stellate cells were treated with CGS-12680 at various concentrations with or without the addition of 10 micro-M adenosine $A_{2A}$ receptor antagonist CSC following pulsing with $^{14}$C-proline. The collagen was extracted by ethanol precipitation and quantified following phosphorimager exposure. As shown in FIG. 3, the adenosine $A_{2A}$ receptor agonist CGS-21680, dramatically increased collagen production by 3223±917% over control at a concentration of 10 mM (n=6, p<0.001).

The CGS-21680-induced increase in collagen production was almost completely abrogated by preincubation with the adenosine $A_{2A}$ receptor antagonist, 8-(3-chlorostyryl)-caffeine (CSC) for four hours at 37° C., 5% $CO_2$, as shown in FIG. 3. The adenosine $A_1$ antagonist, 8-cyclopentyldipropylxanthine (DPCPX), and the $A_{2B}$ receptor antagonist, enprofylline, had minimal inhibitory effects on the potentiation of collagen release (data not shown).

Another experiment demonstrated that CGS-21680 at concentrations up to 100 nM also increased collagen production in immortalized human hepatic stellate cells (LX-1) in a dose dependent manner that was blocked by CSC, as shown in FIG. 3. At CGS-21680 concentrations above 100 nM, collagen production by LX-1 decreases. Since $A_{2A}$ receptor selectivity of CGS-21680 decreases with increasing concentration, and recruitment of $A_{2B}$ receptor activity is observed with CGS-21680 concentrations above 100 nM, agonistic effects in $A_{2B}$ receptors by high-dose CGS-21680 is likely to be responsible for the decrease in collagen production. This is consistent with Dubey's observations on cardiac fibroblasts that adenosine $A_{2B}$ receptor activation decreases collagen synthesis, Dubey et al., *Hypertension* 1998; 31(4):943–8. Alternatively, CGS-21680-induced changes in collagen production may be the result of alterations in the expression of collagenase/metalloproteinases (MMP) or their inhibitors, tissue inhibitors of metalloproteinases, TIMP. Adenosine, acting through one of its receptors, most likely the $A_{2B}$ receptor, has been noted to alter metalloproteinase expression (Boyle et al., *Arthritis Rheum* 1996:39(6):923–30.

Figure 5:
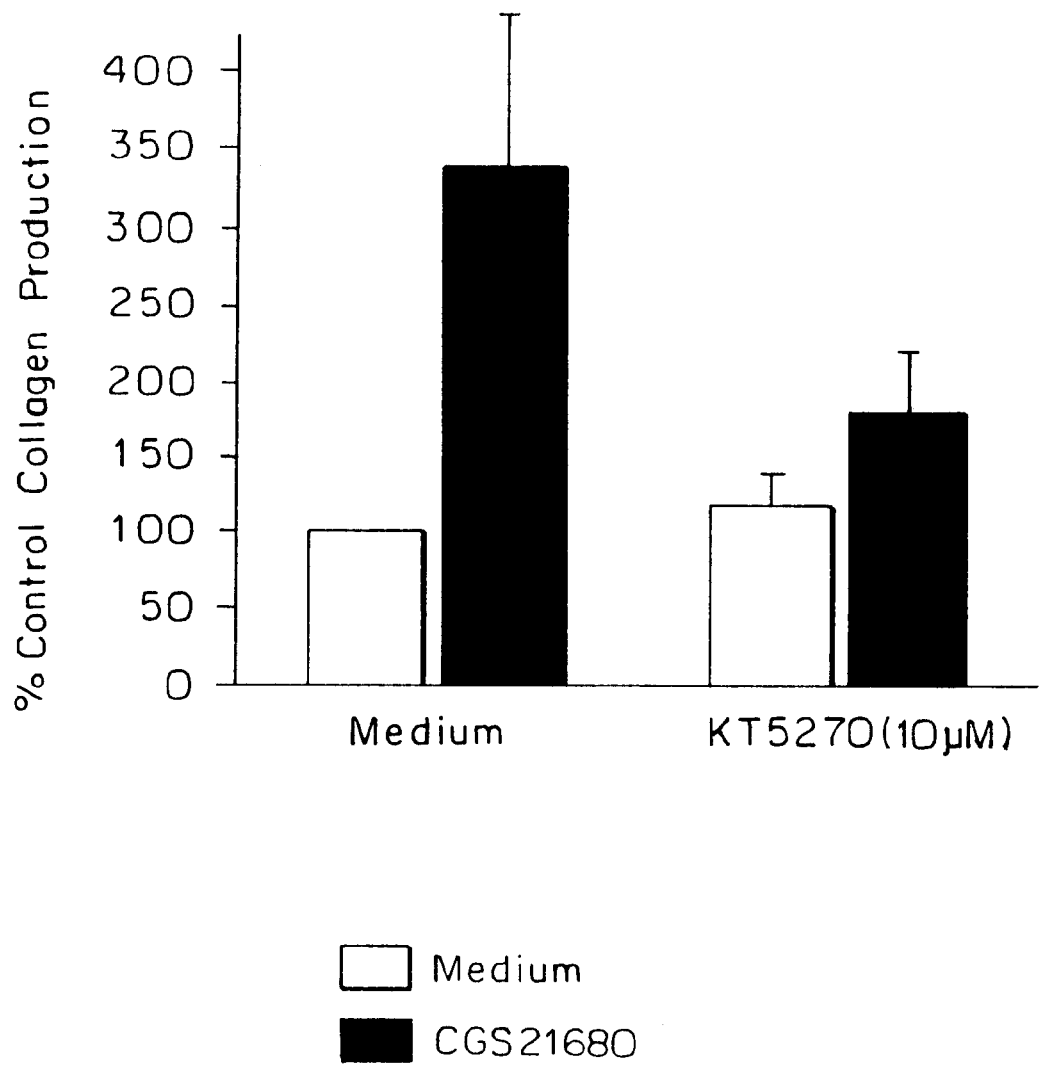
FIG. 5 shows that KT-5720, a protein kinase A inhibitor, abrogates the CGS-21680-mediated increase in collagen production by rHSC.
Figure 7A:
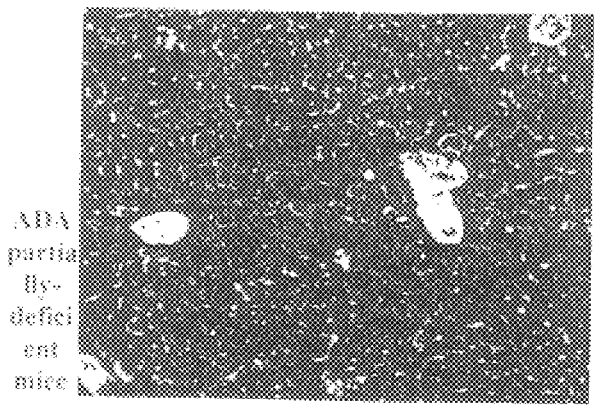
FIG. 7 illustrates with photomicrographs that adenosine deaminase partially-deficient mice develop liver fibrosis.
Figure 7B:
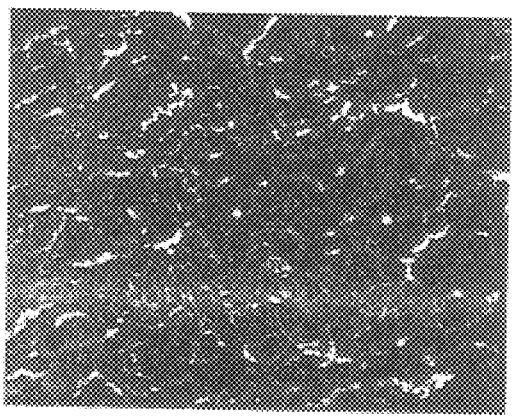
Figure 7C:
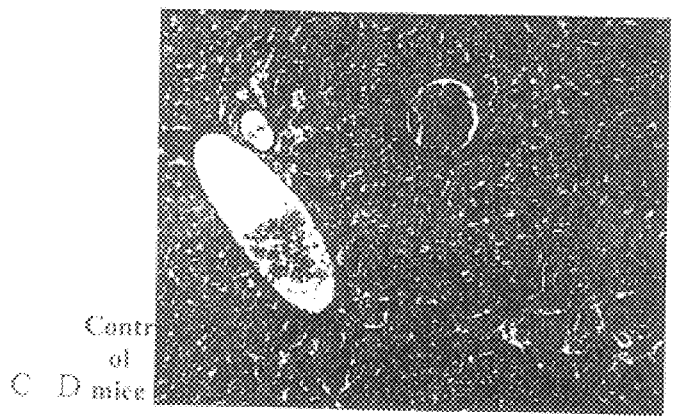
Figure 7D:
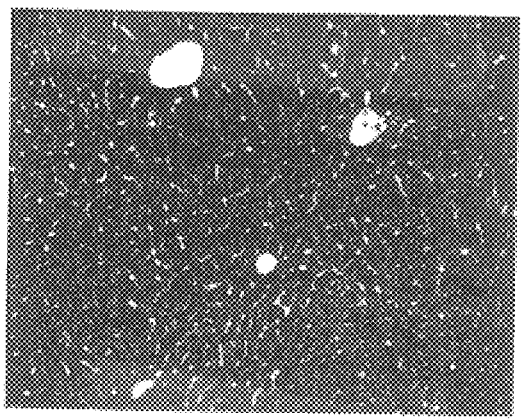

KT-5720, a Protein Kinase A Inhibitor, Abrogates the CGS-218680-mediated Increase in Collagen Production by rHSC The cAMP/protein kinase A pathway is known to mediate adenosine $A_{2A}$ receptor signal transduction. The effect of protein kinase A inhibition was studied on CGS-21680- mediated collagen production in rHSC. Rat HSC were treated with 10 micromolar CGS-21680 for four hours at 37° C., 5% $CO_2$, with or without the addition of 10 micromolar KT-5720, a protein kinase A inhibitor, and collagen production was extracted by ethanol precipitation and quantified following phosphoimager exposure. KT-5720 was found to suppress the CGS-21680-mediated increase in collagen production by 47%, from 339±99% of control collagen production to 181±69% of control, n=4, p<0.013, as shown in FIG. 5. The CGS-21680-induced increase in collagen production therefore occurs at least on part through the cAMP/protein kinase A pathway.

Adenosine $A_{2A}$ Receptor-deficient Mice are Protected Against Carbon Tetrachloride-induced Liver Fibrosis The adenosine $A_{2A}$ receptor has been found to mediate collagen production in cell culture models. Studies were conducted to determine whether adenosine $A_{2A}$ receptor-deficient mice would be protected against cirrhosis using the carbon tetrachloride model of liver fibrosis. C57BL/6 mice deficient for either the adenosine $A_{2A}$ ($A_{2A}$-/-) or $A_3$ ($A_3$-/-) receptor (gift of Dr. J. F. Chen and Dr. M. A. Jacobson) were treated with 0.05 ml carbon tetrachloride in oil, 50:50 v:v, subcutaneously, twice weekly, n=5, for each group, for four weeks. The animals were then sacrificed, and histological grading of liver fibrosis was undertaken using the Roenigk scale. All five $A_3$-/- mice developed Roenigk grade 3 fibrosis of the liver after four weeks, while all five $A_{2A}$-/- mice showed almost no sign of fibrosis, Roenigk grade 0, as shown in FIG. 6. Four of the wild type controls for the $A_{2A}$-/- mice succumbed to carbon tetrachloride toxicity early, within three to ten days, and autopsies showed massive hepatic necrosis and steatosis in all four animals. The only survivor of this group showed gross evidence of fibrosis.

Studies were conducted to determine whether adenosine $A_{2A}$ receptor-deficient mice would be protected against fatty liver using the carbon tetrachloride model of liver fibrosis. C57BL/6 mice deficient for either the adenosine $A_{2A}$ ($A_{2A}$-/-) or $A_3$ ($A_3$-/-) receptor (gift of Dr. J. F. Chen and Dr. M. A. Jacobson) were treated with 0.05 ml carbon tetrachloride in oil, 50:50 v:v, subcutaneously, twice weekly, n=5, for each group, for four weeks. The animals were then sacrificed, and histological grading of fatty liver was undertaken. All five $A_3$-/- mice developed fatty liver after four weeks, while all five $A_{2A}$-/- mice showed almost no sign of fatty liver.

Adenosine Deaminase Partially-deficient Mice Develop Hepatic Fibrosis

Adenosine deaminase (ADA) is an essential enzyme for purine metabolism that is responsible for the hydrolytic deamination of adenosine and 2'-deoxyadenosine to inosine and 2'-deoxyinosine, respectively (Frederiksen et a;/. *Arch. Biochem. Biophys* 1966; 113(2):383–8. Deficiency of ADA leads to accumulation of adenosine in the circulation and tissues, Hirschhorn, *Clin. Immunol. Immunopathol* 1995; 76(3 Pt2):S219–27.

As reported in Blackburn et al., *J Exp Med* 2000: 192(2): 159–70 and *J Biol Chem* 2000, Dr. M. Blackburn has generated and genotyped ADA-deficient mice that develop severe combined immunodeficiency and pulmonary inflammation, leading to death at three weeks of age. More recently, Dr. Blackburn's laboratory has developed mice that are partially ADA-deficient, and which exhibit ectopic expression of the transgene used to rescue them from prenatal lethality. The ADA partially deficient mice live for four to five months, but die from apparent respiratory distress. Unlike the completely ADA-deficient mice, these animals develop severe lung fibrosis which contributes to a progressive loss of lung function. ADA partially-deficient mice also spontaneously develop varying degrees of liver fibrosis during their lifetime. At 2.5 months of age, some inflammation and fibrosis is seen in the liver. By four months of age, all five of the ADA partially-deficient mice examined showed increased liver inflammation and fibrosis, as shown in FIG. 7. Fibrosis develops around blood vessels as well as in the parenchyma. The liver capsule is also thicker in the ADA partially-deficient mice. Since they exhibit fibrosis in the pulmonary parenchyma as well, and pulmonary adenosine levels have been found to be much higher in ADA partially-deficient mice compared to control mice (11.904+ 2.263 nmoles adenosine/mg protein vs. 0.0324+0.067 nmoles adenosine/mg protein at 12 weeks, ADA partially-deficient vs. control, n=4 and n=5, respectively, it is likely that perturbations in adenosine homeostasis are the cause of the resulting phenotypes.

FIG. 7 shows histological sections of mice partially deficient for ADA stained with trichrome and adenosine deaminase. Partially-deficient mice exhibit clear fibrosis, upper panels A and B, that is not seen in control mice, lower panels C and D.

A number of experiments were conducted which demonstrated that CGS-21680, a relatively selective adenosine $A_{2A}$ receptor agonist, promotes collagen synthesis and release from a cultured rat stellate cell line in a dose-dependent fashion (EDC50 approximately 300 nM) by as much as 20-fold (p<0.004). CSC, a specific adenosine $A_{2A}$ receptor antagonist, almost completely blocks the CGS-21680-mediated promotion of collagen synthesis and release.

DPCPX, an adenosine $A_1$ receptor antagonist, and enprofylline, an $A_{2B}$ receptor antagonist, have little effect on the capacity of CGS-21680 to stimulate collagen release and synthesis.

The most feared sequel of treatment with methotrexate is hepatic fibrosis. Fortunately, this is an uncommon occurrence in patients with rheumatoid arthritis. Alcohol use is a significant risk factor for development of hepatic fibrosis in patients taking methotrexate. The present inventors have previously demonstrated that methotrexate induces adenosine release from a variety of cell types. FIG. 1, which is representative of two experiments, shows that methotrexate similarly promotes adenosine release from the hepatoma cell line HepG2. The effect of methotrexate on adenosine release is greatly magnified when the cells are also exposed to ethanol (80 mg/dl is the legal limit for driving in most jurisdictions).

Fatty liver is a condition in which there is a fatty transformation of hepatocytes often associated with inflammation and destruction of hepatic parenchyma. Fatty liver may result from exposure to a variety of toxins, including alcohol, drugs or environmental toxins, infectious agents such as hepatitis B and C, inborn errors of metabolism (hemochromatosis), other illnesses such as diabetes mellitus and obesity, or may be idiopathic in origin. The mechanism of fatty transformation remains incompletely understood in all of these conditions, and there is no specific therapy for this condition that is currently available.

Adenosine $A_{2A}$ receptor antagonists, or compounds which inhibit adenosine $A_{2A}$ receptor for activation, are administered to patients with conditions known to cause hepatic fibrosis, cirrhosis and/or fatty liver to prevent development of hepatic fibrosis, cirrhosis and/or fatty liver with incumbent complications. Additionally, adenosine $A_{2A}$ receptor antagonists are administered to patients with established fibrosis, cirrhosis, and/or fatty liver to prevent further fibrosis.

Thus, the present invention is directed to a method for treating or preventing hepatic fibrosis, cirrhosis, and/or fatty liver in a subject comprising administering to the subject at least one agent which inhibits stimulation of the adenosine $A_{2A}$ receptor. Thus at least one agent is preferably an adenosine $A_{2A}$ receptor antagonist or a promotor of adenosine uptake or metabolism.

Adenosine $A_{2A}$ receptor antagonists useful in the above methods are selected from the group consisting of adenosine, 4-{2-[7-amino-2-(2-furyl)(1,2,4)triazolo[2,3-a][1,3,5]triazin-5-ylamino]ethyl}phenol, also known as ZM 241385, 2-phenylaminoadenosine, 2-para-2-carboxyethylphenylamino-5'-N-ethylcarboxamidoadenosine, 5'-N-ethylcarboxamidoadenosine, 5'-N-cyclopropyladenosine, 5'N-methylcarboxamidoadenosine, 8-(3-chlorostyryl)caffeine, and PD-125944 (for chemical structure, see Bruns, R. F. *Annals of New York Academy of Science* 603:211–216, 1990, at page 216).

Other adenosine $A_{2A}$ receptor antagonists that can be used to treat or prevent hepatic fibrosis and/or cirrhosis include 1,3-dipropyl-8-phenylxanthine and 4-{2-[7-amino-2-(2-furyl)[1,2,4]-triazolo[2,3-a][1,3,5]-triazin-5-ylamino]ethyl}phenol (ZM 241385).

Additional adenosine $A_{2A}$ receptor antagonists that can be used to treat or prevent hepatic fibrosis and/or cirrhosis include 8-styryl derivatives of 1,3-7-alkylxanthines of the following formula:

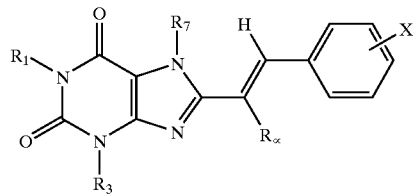

Wherein

R1 and R3 can be methyl, ethyl, propyl, or allyl;

R7 is H, methyl, or C12–C8 alkyl;

R is hydrogen.

Other adenosine $A_{2A}$ receptor antagonists which can be used for treating or preventing hepatic fibrosis and/or cirrhosis include compounds of the following formulae:

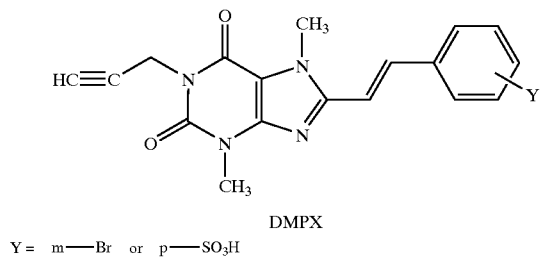

DMPX

Y = m—Br or p—SO$_3$H wherein is m-Br or p-SO3H

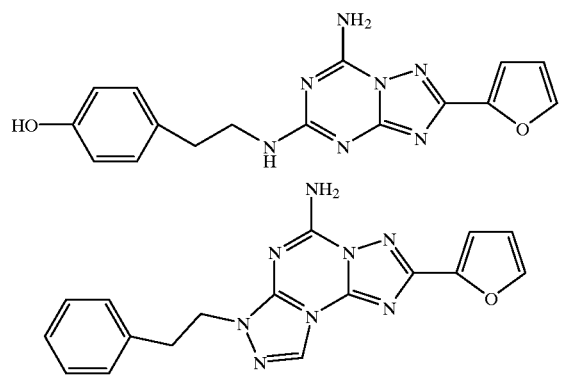

The present invention is further directed to a pharmaceutical composition for treating and/or preventing hepatic fibrosis, cirrhosis, and/or fatty liver comprising:

(a) at least one agent which inhibits activation of the adenosine $A_{2A}$ receptor; and (b) a pharmaceutically acceptable carrier or excipient.

In the above pharmaceutical compositions, the at least one agent is preferably an adenosine $A_{2A}$ receptor antagonist.

The preferred animal subject of the present invention is a mammal, and particularly a human. The terms treating and preventing mean administering to a subject an adenosine $A_{2A}$ receptor antagonist for treating a subject with cirrhosis and/or fibrosis of the liver or fatty liver or for treating a subject with a condition known to cause cirrhosis and/or fibrosis of the liver and/or fatty liver to prevent development of cirrhosis or fibrosis or fatty liver.

The present invention provides pharmaceutical compositions comprising an effective amount of at least one adenosine $A_{2A}$ receptor antagonist to prevent or treat fibrosis and/or cirrhosis of the liver and/or fatty liver.

The pharmaceutical compositions of the present invention comprising at least one adenosine $A_{2A}$ receptor antagonist may be administered by any means that achieve their intended purposes. Amounts and regimens for the administration of the pharmaceutical compositions can be readily determined by those with ordinary skill in the art of treating liver diseases.

The pharmaceutical agent can be administered by any convenient route, including parenteral, subcutaneous, intravenous, intramuscular, intra peritoneal, or transdermal. Alternatively or concurrently, administration may be by the oral route. The dosage administered depends upon the age, health, and weight of the recipient, kind of concurrent treatment, if any, and the nature of the effect desired.

Compositions within the scope of this invention include all compositions wherein the adenosine $A_{2A}$ receptor antagonist is contained in an amount effective to achieve its intended purpose. While individual needs vary, determination of optimal ranges of effective amounts of each component is within the skill of the art. Typical dosages comprise 0.01 to 100 mg/kg body weight. The preferred dosages comprise 0.1 to 100 mg/kg body weight. The most preferred dosages comprise 1 to 100 mg/kg body weight.

Pharmaceutical compositions for administering the active ingredients of the present invention preferably contain, in addition to the pharmacologically active compound, suitable pharmaceutically acceptable carriers comprising excipients and auxiliaries which facilitate processing of the active compounds into preparations which can be used pharmaceutically. Preferably, the preparations, particularly those preparations which are administered orally and which can be used for the preferred type of administration, such as tablets, dragees, and capsules, and also preparations which can be administered rectally, such as suppositories, as well as suitable solutions for administration by injection or orally, contain from about 0.01 to 99 percent by weight, preferably from about 20 to 75 percent by weight, active compound(s), together with the excipient. For the present invention, all percentages are by weight unless otherwise indicated. In addition to the following described pharmaceutical compositions, the compounds of the present invention can be formulated as inclusion complexes, such as cyclodextrin inclusion complexes or liposomes.

Examples of pharmaceutically acceptable acid addition salts for use in pharmaceutical compositions according to the present invention include those derived from mineral acids, such as hydrochloric, hydrobromic, phosphoric, metaphosphoric, nitric, and sulfuric acids, and organic acids such as tartaric, acetic, citric, malic, lactic, fumaric, benzoic, glycolic, gluconic, succinic, and arylsulfonic, such as p-toluenesulfonic, acids.

The pharmaceutically acceptable carriers include vehicles, adjuvants, excipients, or diluents that are well known to those skilled in the art and which are readily available. It is preferred that the pharmaceutically acceptable carrier be one which is chemically inert to the active compounds and which has no detrimental side effects or toxicity under the conditions of use.

The choice of carrier is determined partly by the particular active ingredient, as well as by the particular method used to administer the composition. Accordingly, there is a wide variety of suitable formulations of the pharmaceutical compositions of the present invention. Formulations can be prepared for oral, aerosol, parenteral, subcutaneous, intravenous, intra arterial, intramuscular, intra peritoneal, intra tracheal, rectal, and vaginal administration.

Suitable excipients are, in particular, fillers such as saccharides, for example, lactose or sucrose, mannitol or sorbitol, cellulose preparations and/or calcium phosphates, for example, tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone.

Suitable formulations for parenteral administration include aqueous solutions of the active compounds in water-soluble form, such as water-soluble salts. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances which increase the viscosity of the suspension such as, for example, sodium carboxymethyl cellulose, sorbitol, and/or dextran. Optionally, the suspension may also contain stabilizers.

Other pharmaceutically acceptable carriers for the adenosine $A_{2A}$ receptor antagonist according to the present intention are liposomes, pharmaceutical compositions in which the active ingredient is contained either dispersed or variously present in corpuscles consisting of aqueous concentric layers adherent to lipid layers. The active ingredient may be present both in the aqueous layer and in the lipidic layer, inside or outside, or, in any event, in the nonhomogeneous system generally known as a liposomic suspension.

The hydrophobic layer, or lipidic layer, generally, but not exclusively, comprises phospholipids such as lecithin and sphingomyelin, steroids such as cholesterol, more or less ionic surface active substances such as dicetylphosphate, stearylamine or phosphatidic acid, and/or other materials of a hydrophobic nature.

The compounds may also be formulated for transdermal administration, for example, in the form of transdermal patches so as to achieve systemic administration.

Formulations suitable for oral administration can consist of liquid solutions such as effective amounts of the compound(s) dissolved in diluents such as water, saline, or orange juice; capsules, tablets, sachets, lozenges, and troches, each containing a predetermined amount of the active ingredient as solids or granules; powders; suspensions in an appropriate liquid; and suitable emulsions. Liquid formulations may include diluents such as water and alcohols, e.g., ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscaramellose sodium, talc, magnesium stearate, calcium stearate, zinc stearate, stearic acid, and other preservatives, flavoring agents, and pharmaceutically acceptable disintegrating agents, moistening agents, preservatives, flavoring agents, and pharmacologically compatible carriers. Lozenge forms can comprise the active ingredient in a carrier, usually sucrose and acacia or tragacanth, as well as pastilles comprising the active ingredient in an inert base such as gelatin or glycerin, or sucrose and acacia. Emulsions and the like can contain, in addition to the active ingredient, such carriers as are known in the art.

Formulations suitable for parenteral administration include aqueous and non-aqueous isotonic sterile injection solutions which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compounds can be administered in a physiologically acceptable diluent in a pharmaceutical carrier, such as a sterile liquid or mixture of liquids, including water, saline, aqueous dextrose and related sugar solutions, an alcohol such as ethanol, isopropanol or hexadecyl alcohol, glycols such as propylene glycol or polyethylene glycol, glycerol ketals such as 2,2-dimethyl-1,3-dioxolane-4-methanol, ethers such as poly(ethyleneglycol) 400, oils, fatty acids, fatty acid esters or glycerides, or acetylated fatty acid glycerides, without the addition of a pharmaceutically acceptable surfactant, such as soap or a detergent, suspending agents, such as carbomers, methylcelluolose, hydroxypropylmethylcellulose, or carboxymethylcellulose, or emulsifying agents and other pharmaceutical adjuvants.

Oils which can be used in parenteral formulations include petroleum, animal, vegetable, or synthetic oils. Specific examples of oils include peanut, soybean, sesame, cottonseed, corn, olive, petrolatum, and mineral. Fatty acids can be used in parenteral formulations, including oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include cationic detergents such as dimethyl dialkyl ammonium halides, and alkyl pyridimium halides; anionic detergents such as dimethyl olefin sulfonates, alkyl, olefin, ether, and monoglyceride sulfates and sulfosuccinates; nonionic detergents such as fatty amine oxides, fatty acid alkanolamides, and polyoxyethylenepolypropylene copolymers; amphoteric detergents such as alkyl-beta-aminopropionates and 2-alkyl-imidazoline quaternary ammonium salts; and mixtures thereof.

Parenteral formulations typically contain from about 0.5 to about 25% by weight of the active ingredient in solution. Suitable preservatives and buffers can be used in these formulations. In order to minimize or eliminate irritation at the site of injection, these compositions may contain one or more nonionic surfactants having a hydrophilic-lipophilic balance (HLB) of from about 12 to about 17. The quantity of surfactant in such formulations ranges from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be present in unit dose or multiple dose sealed containers, such as ampules and vials, and can be stored in a freeze-dried (lyophilized) condition requiring only the addition of the sterile liquid carrier, e.g., water, for injections immediately prior to use. Extemporaneous injection solutions and suspensions can be prepared from sterile powders, granules, and tablets of the kind previously described.

Additionally, the adenosine $A_{2A}$ receptor antagonists can be made into suppositories by mixing the active ingredient with a variety of bases, including emulsifying bases or water-soluble bases. Formulations suitable for vaginal administration may be in the form of pessaries, tampons, creams, gels, pastes, foams, or spray formulations containing, in addition to the adenosine $A_{2A}$ receptor antagonists, such carriers as are known in the art to be appropriate.

The adenosine $A_{2A}$ receptor antagonists can be used as functionalized congeners for coupling to other molecules, such as amines and peptides. The use of such congeners provides for increased potency, prolonged duration of action, and prodrugs. Water solubility is also enhanced, which allows for reduction, if not complete elimination, of undesirable binding to plasma proteins and partition into lipids. Accordingly, improved pharmacokinetics can be realized.

Suitable methods of administering an adenosine $A_{2A}$ receptor antagonist to a subject are available. Although more than one route can be used to administer a particular compound, a particular route can provide a more immediate and more effective reaction than another route. Accordingly, the above-described methods are merely exemplary and are in no way limiting.

Any of a number of ligand binding assays well known in the art may be used to test whether a particular agent suspected of being an adenosine $A_{2A}$ receptor antagonist indeed binds to the receptor and mediates the expected biochemical or biological activity, such as stimulation of adenylyl cyclase activity. Assays such as radioligand binding and measurement of agonist induced biochemical changes are disclosed in a number of references, e.g., Van Calker et al., *J. Neurochem.* 33:999–1005, 1979 and Stiles, *Trends in Pharmacol. Sci.* 7:486–490, 1986. Also, binding or functional assays using transfected or expressed adenosine $A_{2A}$ receptor agonists can also be used to test whether a particular agent indeed binds to the receptor.

A well-known assay method is based on using a ligand or agonist which is capable of binding to and activating both the $A_{2A}$ and $A_{2B}$ subtypes of adenosine receptors. In this approach, a displacer compound which occupies any adenosine $A_{2B}$ receptors is used, which leaves $A_{2A}$ receptors available for binding and activation. This technique is described in Bruns, U.S. Pat. No. 4,705,658, which patent is hereby incorporated by reference in its entirety.

Similar amounts of adenosine $A_{2A}$ receptor antagonists or adenosine uptake promoters are used for prevention and treatment of hepatic fibrosis or cirrhosis or fatty liver. Treatment is continued based upon the condition of the patient and response to the treatment, which can readily be determined by one skilled in the art without undue experimentation.

Administration of adenosine $A_{2A}$ receptor antagonists or adenosine uptake promotor is particularly useful in treating victims of poisoning, such as by tetrachloromethane, as well as patients suffering from viral infections, autoimmune diseases, and primary biliary cirrhosis.

Having now fully described this invention, it will be appreciated by those skill in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the invention following, in general, the principles of the intention and including such departures from the present disclosure as come within known or customary practice within the art to which the invention pertains and as may be applied to the essential features hereinbefore set forth as follows in the scope of the appended claims.

REFERENCES

Anand-Srivastava, M. B. et al., *Biochem. Phys. Res. Commun.* 108:213–219 (1982).
Anand-Srivastava, M. B. et al., *Life Sci.* 37:857–867 (1985).
Barrington, W. W. et al., *Mol. Pharmacol.*, 38:177–183 (1990).
Barrington, W. W. et al., *Proc. Natl. Acad. Sci. USA* 86:6572–7576 (1989).
Berne, R. M., *Circ. Res.*, 47:807–813 (1980).
Bruns, U.S. Pat. No. 4,705,658.
Burnstock et al., *Cell Membrane Receptors of Drugs and Hormones.*
Cronstein, B. N. et al., *J. Immnol.*, 135:1366–1371 (1985).
Cronstein, B. N. et al., *J. Immnol.*, 148:2201–2206 (1985).
Cronstein, B. N. et al., *J. Clin. Invest.*, 78:760–770 (1986).
Cronstein, B. N. et al., supra.
Cronstein, B. N. et al., *Proc. Natl. Sci USA*, 88:2441–2445 (1991).
Cronstein et al., U.S. Pat. No. 5,932,558.
Herlihy, J. T. et al., *Am. J. Physiol.*, 230:1239–1243 (1976).
Hutchinson, U.S. Pat. No. 4,968,697.
Hutchinson, U.S. Pat. No. 5,063,233.
Iannone, M. A. et al., *Fed. Proc.*, 44:580 (abstr.) (1985).
Jacobson, K. A. et al., *J. Med. Chem.*, 35:407–422 (1992).
Jarvis, M. R. et al., *J. Pharmacolo. Exp. Their,* 251:888–893 (1989).
Khakh et al., *Trends in Pharmacological Sciences* 19(2): 39–41 (1998).

Klatsky et al., "Alcohol, Smoking, Coffee, and Cirrhosis", *American Journal of Epidemiology* 136(10):1248–1257 (1992).
Klatsky et al., "Coffee, Tea and Immortality", *Annals of Epidemiology*, 3(4):375–381 (1993).
Lepore, A. R. et al., "The Effect of Drinking Coffee and Smoking Cigarettes on the Risk of Cirrhosis Associated with Alcohol Consumption", *European Journal of Epidemiology*, 10(6):657–664 (1994).
Liang et al., U.S. Pat. No. 5,859,019.
Londos, C. et al., *Proc. Natl. Acad. Sci. USA*, 77:2552–2554 (1980).
Noris, J. S. et al., *Nature*, 248:422–424 (1974).
Poulsen et al., *Bioorganic & Medicinal Chemistry*, 6(6):619–41 (1998).
Ralevid et al., *Pharmacological Reviews*, 503(3):413–92 (1998).
Ramkumar, V. et al., *Anu. Rev. Physiol.*, 54:211–225 (1992).
Ramkumar, V. et al., *Molec. Pharmacol.* 37:149–156 (1990).
Ramkumar, V. et al., Supra.
Roberts, P. A. et al., *Biochem H.*, 227669–674 (1985).
Rose. F. R. et al., *J. Exp. Med.* 167:1186–1194 (1989).
Salmon, J. E., *Immuno*, 145:2235–2240 (1990).
Schrier, D. J. et al., *J. Immunol.*, 137:3284–3289 (1989).
Stiles G. L., *J. Biol. Chem*, 267:6451–6454 (1992).
Stiles G. L., *Trends in Pharmacol. Sci.* 7:486–490 (1986).
Straub et al., eds., Raven Press, New York, pp. 107–118 (1978).
Tanaka et al., "Coffee Consumption and Decreased Serum Gamma-Glutamyltransferase and Aminotransferase Activities Among Male Alcohol Drinkers", *International Journal of Epidemiology*, 27(3):438–443, (1998).
Van Calker, D. et al., *J. Neurochem*, 33:999–1005 (1979).
Smail, E. H., et al., "In vitro, Candida albicans releases the immune modulator adenosine and a second, high-molecular weight agent that blocks neutrophil killing," *J. Immunol.* 148(11):3588–3595 (1992).
Puig, J. G., et al., "Ethanol-induced activation of adenine nucleotide turnover. Evidence for a role of acetate." *J. Clin. Invest.* 74(3):936–941 (1984).
Dubey, R. K., et al., "Adenosine inhibits collagen and protein synthesis in cardiac fibroblasts: role of A2B receptors." *Hypertension* 31(4):943–948 (1998).
Boyle, D. L., et al., "Inhibition of synoviocyte collagenase gene expression by adenosine receptor stimulation." *Arthritis Rheum* 39(6):923–930 (1996).
Chen, J. F., et al., "A(2A) adenosine receptor deficiency attenuates brain injury induced by transient focal ischemia in mice." *J. Neurosci.* 19(21):9192–9200 (1999).
Salvatore, C. A., et al., "Disruption of the A(3) adenosine receptor gene in mice and its effect on stimulated inflammatory cells." *J. Biol. Chem.* 275(6):4429–4434 (2000).
Frederiksen, S., "Specificity of adenosine deaminase toward adenosine and 2'-deoxyadenosine analogues." *Arch Biochem Biophys* 113(2):383–388 (1966).
Hirschhorn, R., "Adenosine deaminase deficiency: molecular basis and recent developments." *Clin. Immunol. Immunopathol.* 76(3 Pt 2):S219–227 (1995).
Blackburn, M. R., et al., "Metabolic consequences of adenosine deaminase deficiency in mice are associated with defects in alveogenesis, pulmonary inflammation, and airway obstruction." *J Exp Med* 192(2):159–170 (2000).
Blackburn, M. R., et al., "The use of enzyme therapy to regulate the metabolic and phenotypic consequences of adenosine deaminase deficiency in mice: Differential impact on pulmonary and immunologic abnormalities." *J. Biol Chem* (2000).

What is claimed is:

1. A method for preventing development of hepatic fibrosis or cirrhosis or fatty liver comprising administering to a subject in need thereof an effective amount of at least one adenosine $A_{2A}$ receptor antagonist.

2. The method according to claim 1 wherein the adenosine $A_{2A}$ receptor antagonist is selected from the group consisting of adenosine, 2-phenylaminoadenosine, 2-p-2-carboxyethylphenylamino-5'-N-ethylcarboxamidoadenosine, 5-N-ethylcarboxamidoadenosine, 5'-N-cyclopropyladenosine, 5'-N-methylcarboxamidoadenosine, 8-(3-chlorostyryl)caffeine, 1,3-dipropyl phenylxanthine and 4-{2-[7-amino-2-(2-furyl)[1,2,4]-triazolo[2,3-a][1,3,5]-triazin-5-ylamino]ethyl}phenol (ZM 241385), 8-styryl derivatives of 1,3-7-alkylxanthines of the following formula:

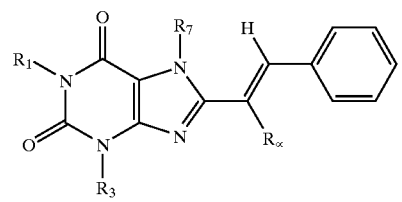

wherein
$R_1$ and $R_3$ are methyl, ethyl, propyl, or allyl;
$R_7$ is H, methyl, or $C_1$–$C_8$ alkyl;
R is hydrogen; and compounds of the following formula:

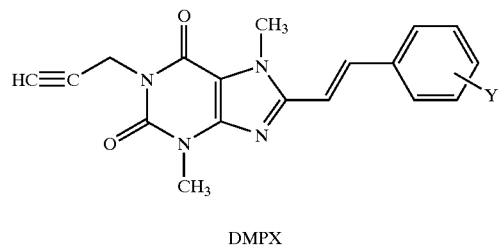

DMPX wherein Y=m-Br or p-$SO_3H$.

3. A method for treating hepatic fibrosis or cirrhosis or fatty acids comprising administering to a subject in need thereof an effective amount of at least one adenosine $A_{2A}$ receptor antagonist or at least one adenosine uptake promotor.

4. The method according to claim 3 wherein the adenosine $A_{2A}$ receptor antagonist is selected from the group consisting of

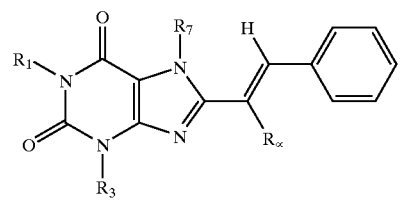

wherein

R₁ and R₃ are methyl, ethyl, propyl, or allyl;

R₇ is H, methyl, or $C_1$–$C_8$ alkyl;

R is hydrogen; and compounds of the following formula:

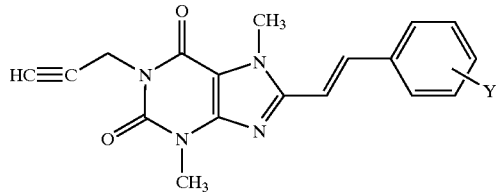

DMPX wherein Y=m-Br or p-SO₃H.

5. The method according to claim 4 wherein the adenosine $A_{2A}$ receptor antagonist is selected from the group consisting of 8-(3-chlorostyryl) caffeine and 4-{2-[7-amino-2-(2-furyl)(1,2,4)triazolo[2,3-a][1,3,5]triazin-5-ylamino]ethyl}phenol, also known as ZM 241385.

6. A method for preventing development of hepatic fibrosis, cirrhosis, or fatty liver comprising administering to a subject in need thereof an effective amount of at least one agent which inhibits stimulation of the adenosine $A_{2A}$ receptor.

7. A method for treating hepatic fibrosis or cirrhosis or fatty liver comparing administering to a subject in need thereof an effective amount of at least one agent which inhibits stimulation of the $A_{2A}$ receptor.

8. A method for preventing development of fibrosis comprising administering to a subject in need thereof an effective amount of at least one adenosine $A_{2A}$ receptor antagonist.

9. The method according to claim 8 wherein the adenosine $A_{2A}$ receptor antagonist is selected from the group consisting of adenosine, 2-phenylaminoadenosine; 2-p-carboxyethylphenylamino-5'-N-ethylcarboxaminoadenosine; 5-N-ethylcarboxamidoadenosine; 5'-N-cyclopropyladenosine; 5'-N-methylcarboxamidoadenosine; 8-(3-chlorostyryl) caffeine; PD-125944, 1,3-dipropyl phenylxanthine; 4-{2-[7-amino-2-(2-furyl)(1,2,4)-triazolo[2,3-a][1,3,5]-triazin-5-ylamino]ethyl}phenol; 8-styryl derivatives of 1,3,7-alkylxanthines of the formula:

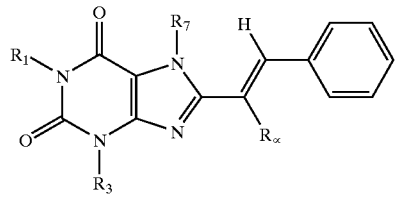

wherein

R₁ and R₃ are methyl, ethyl, propyl, or allyl;

R₇ is H, methyl, or $C_1$–$C_8$ alkyl;

R is hydrogen; and compounds of the formula:

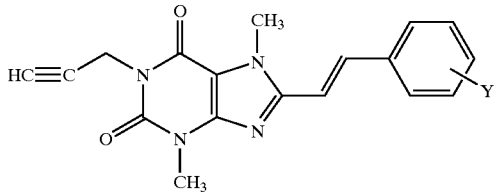

DMPX wherein Y is m-Br or p-SO₃H.

10. A method for treating fibrosis comprising administering to a subject in need thereof an effective amount of at least one adenosine $A_{2A}$ receptor antagonist or at least one adenosine uptake promoter.

11. The method according to claim 10 wherein the adenosine receptor antagonist is selected from the group consisting of

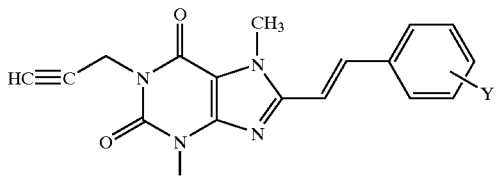

wherein

R₁ and R₃ are methyl, ethyl, propyl, or allyl;

R₇ is H, methyl, or $C_1$–$C_8$ alkyl;

R is hydrogen; and compounds of the following formula:

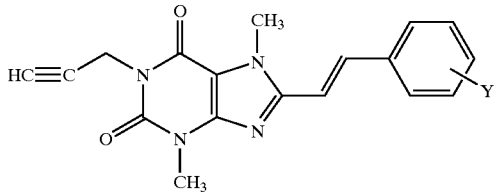

DMPX wherein Y=m-Br or p-SO₃H.

* * * * *